United States Patent
Hirayama et al.

(10) Patent No.: US 7,132,003 B2
(45) Date of Patent: Nov. 7, 2006

(54) AIR CLEAN APPARATUS

(75) Inventors: Shoji Hirayama, Yamato (JP);
Kensuke Hirayama, Yamato (JP)

(73) Assignee: Hirayama Setsubi Kabushiki Kaisha, Yamato (JP)

( * ) Notice: Subject to any disclaimer, the term of this patent is extended or adjusted under 35 U.S.C. 154(b) by 214 days.

(21) Appl. No.: 10/674,474

(22) Filed: Oct. 1, 2003

(65) Prior Publication Data
US 2004/0118094 A1    Jun. 24, 2004

(30) Foreign Application Priority Data
Oct. 4, 2002  (JP) .............................. 2002-292655
Nov. 12, 2002  (JP) .............................. 2002-328582

(51) Int. Cl.
*B01D 35/30*    (2006.01)

(52) U.S. Cl. ..................... 55/472; 55/486; 422/186.3

(58) Field of Classification Search .................. 55/467, 55/472, 482, 486; 96/222, 224, 226, 227; 422/186.3
See application file for complete search history.

(56) References Cited

U.S. PATENT DOCUMENTS

| 4,370,155 A | * | 1/1983 | Armbruster | ................... 96/140 |
| 5,225,167 A | * | 7/1993 | Wetzel | ........................ 96/224 |
| 2003/0010211 A1 | * | 1/2003 | Yu | ................................. 96/16 |

* cited by examiner

*Primary Examiner*—Robert A. Hopkins
(74) *Attorney, Agent, or Firm*—Oliff & Berridge, PLC (57) ABSTRACT

An air clean apparatus including an air intake intended to be located at a lower position in a corner of a room and an air outlet intended to be located at an upper position in the corner of the room, and at least a filter and a blower both inside the air clean apparatus, characterized in that, when the air clean appratus is installed in a room, a given quantity of circulating blowing air, the given quantity is decided according to the height from the floor underneath the air intake and the underside-open area determined on the basis of particles of the maximum size to be eliminated at the air intake.

8 Claims, 3 Drawing Sheets

AIR CLEAN APPARATUS

The present invention relates to an Air clean appratus for use in living rooms, bedrooms and other places in common houses, mansions and so on.

It is generally known that contaminants in air include floating dusts (substances in particles) and gaseous substances. Some of the substances in particles continuously float, and the others sediment or cumulate, depending on the dimensions of the substances in particles. On the other hand, some of the gaseous substances ascend to a ceiling area and stay there, and the others descend to a floor area and stay there, depending on the specific gravities of gaseous substances. In common houses and mansions, air cleaning-up is carried out in a way that an Air clean appratus is installed in a room to use it for cleaning up interior air contaminated with floating dusts such as interior dusts, hyphae and spores of moulds, pollens, feces of ticks, hairs of pet animals and the like. With such an Air clean appratus, air contaminated with interior dusts and the like is cleaned up in a way of passing the contaminated air through a filter set in the Air clean appratus, and the cleaned-up air is fed back to the interior again (See Patent Literatures 1 and 2).

[Patent Literature 1]
Japanese Utility Model Laid-open No. 4-08022 (Page 1, FIG. 1).

[Patent Literature 2]
Japanese Utility Model Laid-open No. 4-50328 (Page 1, FIG. 1)

However, conventional Air clean appratuss are aiming at only cleaning up air that is contaminated mainly with dusts and the like, and they do not sufficiently take care of behavior of dusts that should be eliminated from the air. In addition, such conventional Air clean appratuss have no available means for eliminating gaseous substances. Thus, it is not achievable yet to clean interior air in an ideal manner at present.

Therefore, it is an object of the present invention to provide an Air clean appratus capable of eliminating floating dusts and harmful gaseous substances from air and ventilating cleaned-up air in rooms in common houses and mansions.

Besides, conventional Air clean appratuss have been made in a form of being included in a large box-like frame, and they are used after being installed on a wall or on a floor. Thus, placement of such an Air clean appratus makes room space be reduced substantially, and this has been a drawback.

According to the present invention, from the reason that many of contaminants descend, sediment and cumulate, the Air clean appratus is formed in an elongated shape extending in a direction along the longitudinal axis of the Air clean appratus main body and it is configured such that air around a floor surface is sucked from the under portion of the Air clean appratus and the cleaned-up air is blown out from the upper portion of the Air clean appratus. The Air clean appratus according to the present invention is provided in a shape that may be placed, for example, in the corner of a room so that the placement thereof will not be troublesome from the room space point of view.

According to another aspect of the present invention, there is provided an Air clean appratus that can be placed in a room in common houses and mansions and can eliminate and decompose not only floating dusts but also exhaust gases such as nitrogen dioxide and sulfur dioxide that penetrate from the exterior when interior air is ventilated, or due to draught.

For aiming at achieving the aforementioned object, the present invention provides an Air clean appratus comprising an air intake intended to be located at a lower position of a corner of a room and an air outlet intended to be located at a upper position of the said corner of the room, and at least a filter and a blower both inside the Air clean appratus, characterized in that, when the Air clean appratus is installed in the room, a given quantity of circulating blowing air, the said quantity is decided according to the height from the floor underneath the air intake and the underside open area determined on the basis of the particles of the maximum size to be eliminated at the air intake. The dimension of particles of the maximum size to be eliminated is in a range of 50 to 100 μm, and the height from the floor underneath the air intake is 40 mm or more, as will be described later.

According to another aspect of the present invention, there is provided an Air clean appratus comprising an air intake provided in the vicinity of the lower portion of the Air clean appratus, an air outlet provided in the vicinity of the upper portion of the Air clean appratus, and at least a filter and a blower both inside the Air clean appratus, characterized in that:

the Air clean appratus is installed in standing state, interior air is sucked by the blower through the air intake and cleaned up inside the Air clean appratus, the cleaned air is blown out from the air outlet into the room to thereby circulate the interior air, the Air clean appratus is formed in a longitudinally-elongated shape of which lower portion locates in the vicinity of a floor surface and of which upper portion has such a height that it reaches the vicinity of a ceiling; and inside the Air clean appratus, an anterior filter is provided in the vicinity of the air intake, and a photocatalytic filter adapted to eliminate and decompose contaminants in the sucked air and with an elongated shape extending in a direction along the longitudinal axis of the Air clean appratus is installed between the said anterior filter and the said blower.

According to still another aspect of the present invention, there is provided an Air clean appratus characterized in that:

the Air clean appratus is configured to have a shape whose transverse cross-section is any of fan-shaped, pentangular and triangular, and dimensions in width and height of both sides of the Air clean appratus are at least 180 mm and 2000 mm or less, respectively, for each side.

According to the aspects of the present invention constituted as described above, it is possible to provided an Air clean appratus intended to be installed in a room of common houses and mansions and capable of eliminating and decomposing not only floating dusts such as dusts, hyphae and spores of moulds, and hairs of pet animals but also exhaust gases, such as nitrogen dioxide and sulfur dioxide, generated by automobiles, combustion furnaces, etc. and penetrated into rooms upon ventilation or due to draught. Furthermore, since the Air clean appratus of the present invention is designed in such a shape that it can be installed in a dead space in the corner of a room. Hence, placement of the Air clean appratus of the present invention does not reduce room space so much and will not be an obstacle.

Unlike the ordinary circulation-type Air clean appratuss, the Air clean appratus of the present invention is a vertical-type in which air is sucked from the floor surface area, then cleaned up inside the Air clean appratus, and cleaned-up air is blown out together with a large number of minus ions from the upper part of the Air clean appratus. In this Air clean appratus, not only exhaust gases and cigarette smoke but also formaldehyde, the cause of so-called "sick house", can be decomposed thanks to a photocatalytic filter installed therein.

Additionally, with a synergistic effect of the photocatalytic filter and the minus ions, dusts, moulds, pollens, ticks and other contaminants are eliminated from air, giving a space with pleasant and healthy air. Furthermore, formaldehyde, toluene and the like, which may be a cause of so-called "sick house" will be decomposed and cleaned up by the photocatalytic filter. Again, since there is a tendency that most of contaminants in air descend, sediment and cumulate downwardly, the Air clean appratus according to the present invention is configured to suck air around a floor surface from the underpart of the Air clean appratus and blow out the cleaned-up air from the upper part thereof, and it is configured in a shape that can be placed in the corner of a room so that it will not be an obstacle in the room.

[Embodiments]

Now, some embodiment for carrying out the present invention will be described below with reference to the appended drawings.

DESCRIPTION OF DRAWINGS

Figure 1:
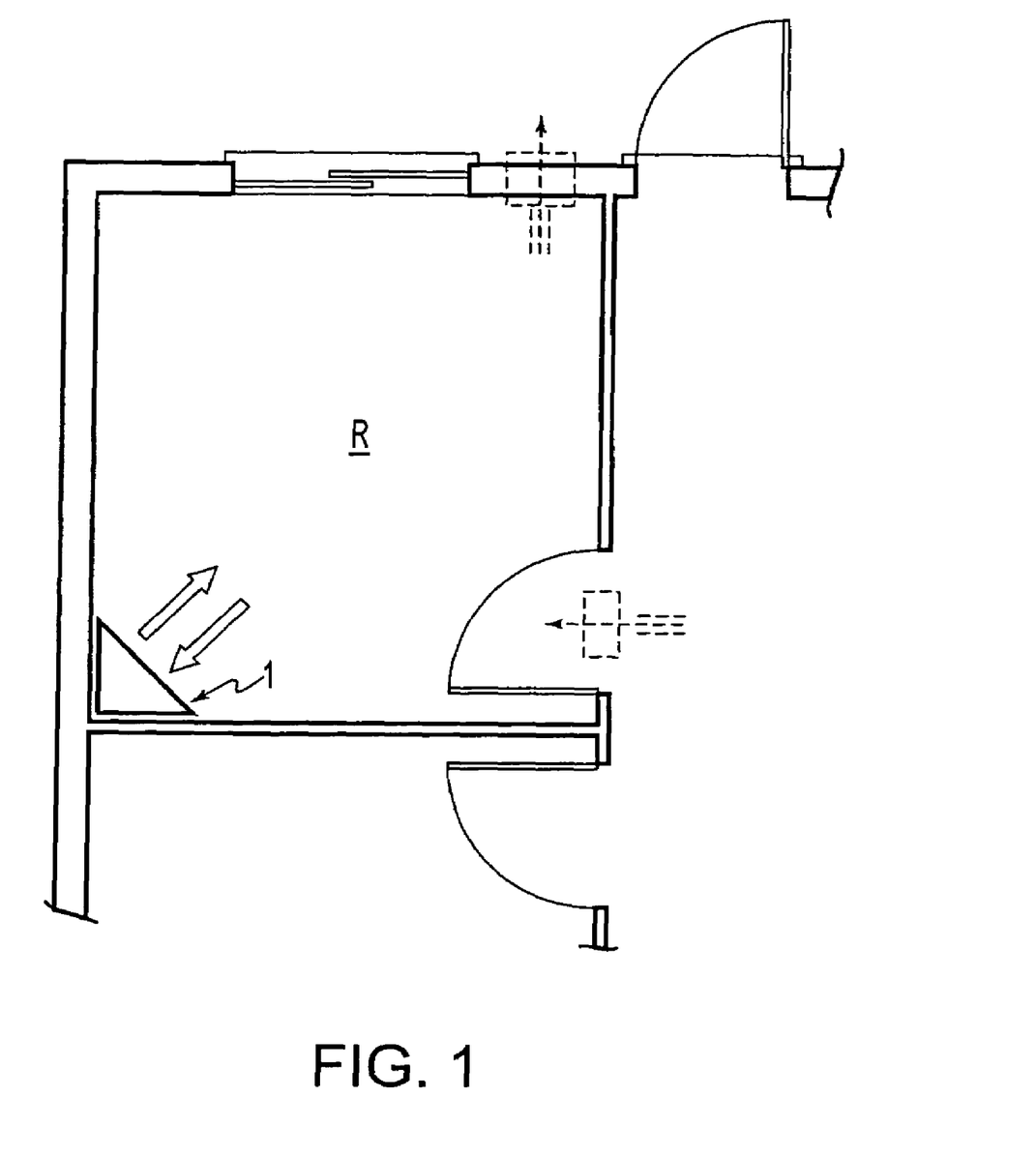
FIG. 1 is a plan view showing an Air clean appratus according to an exemplary embodiment.
Figure 2:
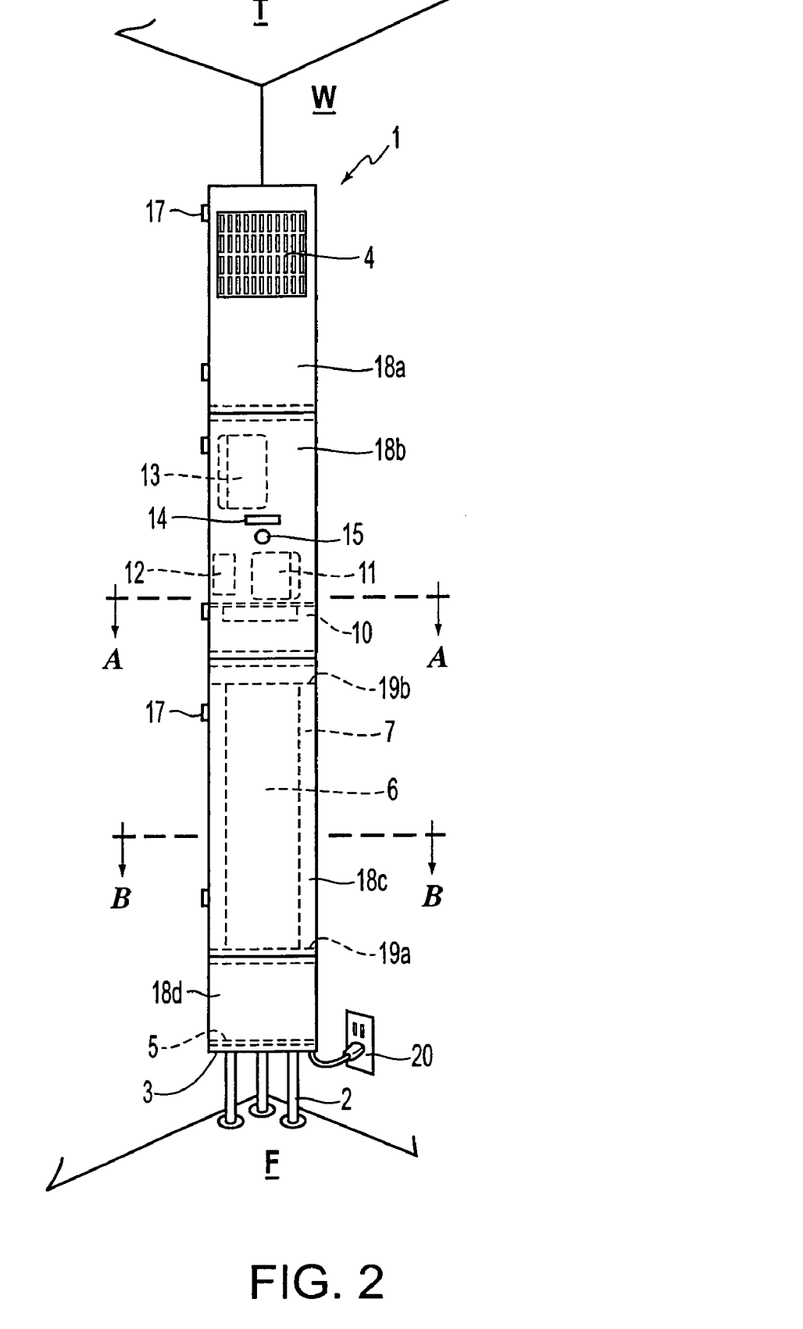
FIG. 2 is a front view of an Air clean apparatus.
Figure 3:
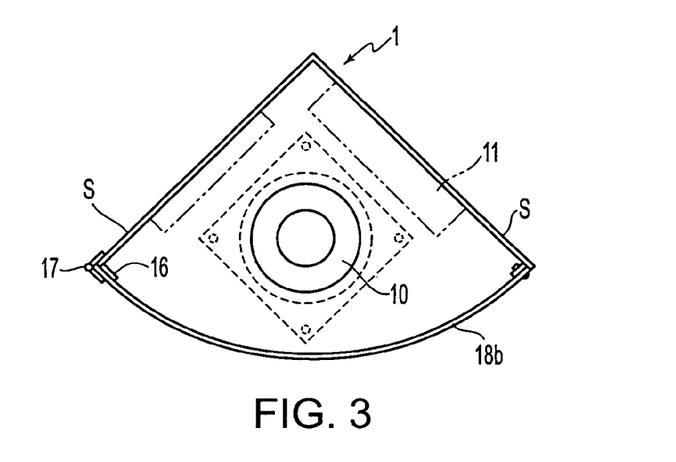
FIG. 3 is a transverse cross-section cut along a line A—A in FIG. 2.

FIG. 1 is a plan showing an Air clean appratus according to an embodiment of the present invention, and FIG. 2 is front view of an Air clean appratus.

The Air clean appratus 1 is supported by legs 2 stood on a floor surface F, and it has such a height that it reaches near a ceiling surface T, of which section is fan-shaped or polygonal and slightly protruding and has a dimension that does not reduce room space so much when the Air clean appratus is placed in the corner surrounded by room walls W. The Air clean appratus 1 is provided with an air intake 3 in the vicinity of the lower end thereof and an air outlet 4 in the vicinity of the upper end thereof, and, inside the Air clean appratus, an anterior filter 5, a photocatalytic filter 6, an ultraviolet lamp 8, a blower 10, etc. are arranged. The Air clean appratus sucks interior air through the air intake 3, cleans up the air, and then blows out the air through the air outlet 4 to circulate the interior air. For protection of the interior hardware, doors or cover plates 18*a*, 18*b*, 18*c* and 18*d* are mounted in a manner that they can be opened and closed with support of several hinges 17, all of those which are provided on the front side of the main body of the Air clean appratus.

Note that FIG. 2 show the Air clean appratus being in a state in which the cover plates 18*c* and 18*d* corresponding to the positions to which the photocatalytic filter 6, the blower 10, etc. are installed are opened so that an operation of maintenance, cleaning or exchange of the photocatalytic filter and blower can be facilitated.

In the embodiment shown in FIG. 2, the Air clean appratus 1 is formed in an elongated tubiform shape, whose upper and lower ends locate in the vicinity of a ceiling face T and in the vicinity of a floor surface F, respectively, and the section of the Air clean appratus is fan-shaped. The Air clean appratus is placed such that the front side of the Air clean appratus 1 does not protrude so much against the room space side. Specifically, the Air clean appratus is formed in an elongated shape such that the maximum width between both sides S, S of the Air clean appratus 1, the said both sides border on wall faces W, respectively, is fixed to 200 mm or less, and preferably 180 mm more or less, and the height H of each the said sides is fixed to 2000 mm or less. However, the dimensions of the said width and height are not limited to those described hereinabove.

Besides, in FIGS. 1 and 2, though it is mentioned that the section of the Air clean appratus is fan-shaped, the section may be formed in either substantially pentangular or triangular (not shown).

Figure 4:
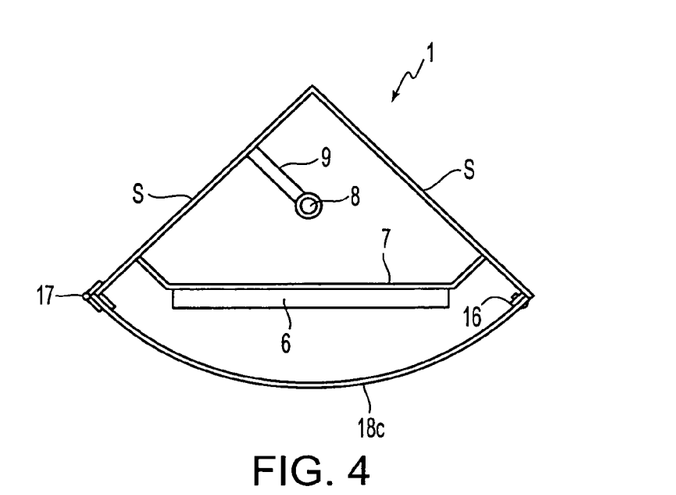
FIG. 4 is a transverse cross-section cut along a line B—B in FIG. 2.

The anterior filter placed to the air intake 3 captures dusts and the like contained in sucked air so that the photocatalytic filter 6 placed in the following stage is prevented from causing clogging up. Furthermore, as shown in FIG. 4 in an enlarged illustration, an elongated photocatalytic filter 6 and a lamp 8 that excites photocatalytic activity, such as an ultraviolet lamp, are arranged in a direction along the longitudinal axis of the Air clean appratus for eliminating and decomposing contaminants in sucked air.

Note that, in the appended figures, reference number 9 is a supporting member for the ultraviolet lamp, 11 is a controller for a blower, 12 is an electrical equipment, 13 is a case for storing a deodorant, 14 is an operation panel, 15 is a display lamp, 16 is a bent front edge of a side wall of the Air clean appratus, and 20 is a convenience outlet.

As shown in FIG. 2, a fixing frame member 7 is fixed in a space that extends in between the side walls S, S of the Air clean appratus and from the upper portion of the anterior filter 5 to the lower portion of the blower 10, and a photocatalytic filter 6 of a sufficient dimension is placed. To the upper and lower space in the reverse side of the fixing frame member, supporting members or brackets are set, to which an ultraviolet lamp, which is a light source for applying light energy to the photocatalytic filter to excite or activate a photocatalyst is fixed (See FIG. 4). Preferred ultraviolet lamp 8 is a bar-shaped lamp that extends in a direction along the longitudinal axis of the Air clean appratus with a distance from the reverse face of the photocatalytic filter 6.

Further, a transverse plate 19*b* that closes the upper front end side of the photocatalytic filter and a transverse plate 19*a* that closes the lower back end side thereof are provided to the fixing frame member 7. Air sucked by the blower through the air intake 3 and the anterior filter 5 pass from the front face of the photocatalytic filter 6 through the layer of the photocatalytic filter to the reverse side thereof and then goes up. Alternately, it may be configured by closing the upper back end side and lower front end side of the photocatalytic filter 9 such that the air penetrates from the back face of the photocatalytic filter 8 through the filter layer and is blown out to the front face of the filter.

With such a configuration, it becomes possible to constitute the Air clean appratus such that air sucked through the air intake 3 at the lower end of the Air clean appratus sufficiently contacts with the photocatalytic filter 6 and is then blown upward inside the Air clean appratus, even though the cross-section of the Air clean appratus is small.

The photocatalytic filter 6 is an air filter prepared by coating a photocatalyst having antimicrobial activity on an unwoven cloth. The primary component of the photocatalyst is titanium oxide. When it absorbs light energy of ultraviolet region, oxidizing activity is activated. With this oxidizing activity decomposes organic substances, that is, contaminants. The photocatalytic filter of this sort is already publicly known, and it is not a special filter.

The contaminants is herein referred to floating dusts, exhaust gases, odors and the like, and the floating dusts is referred to substances in particles that cumulate on a floor in static air, such as dusts, spores and hyphae of moulds, pollens, feces of ticks, hairs of pet animals and so on. The exhaust gases are referred to oxides of nitrogen and sulfur generated by automobiles, combustion furnaces and the like that invade into rooms during ventilation and due to draught. The odors are referred to odors and stenches such as smells deriving from rotten substances, moulds, and pet animals, and totally volatile organic compounds (TVOC) such as formaldehyde that is problematic in recent time in connection with resolution of sick house problem.

As shown in the figure, a blower 10 adapted to suck contaminated air around a floor surface F in a room through the air intake 3 and blow out the air having been cleaned up inside the cleaner from the air outlet 4 is installed over the photocatalytic filter 6.

This blower 10 is configured to blow out a small amount of air so that contaminated air in a room is not stirred by the air blown out through the air outlet 4. Capacity in airflow of the blower used for the Air clean appratus placed in a room of common houses and mansions is enough if it falls within a range of 0.7 to 1.0 m³/min. For example, blowers with the following airflow capacity are preferred.

At 100V×50 Hz, 0.75 cmm (m3/min)×3.3 mm (resistance)×0.32A; or

At 100V×60 Hz, 0.95 cmm (m3/min)×3.3 mm (resistance)×0.27A

Figure 5:
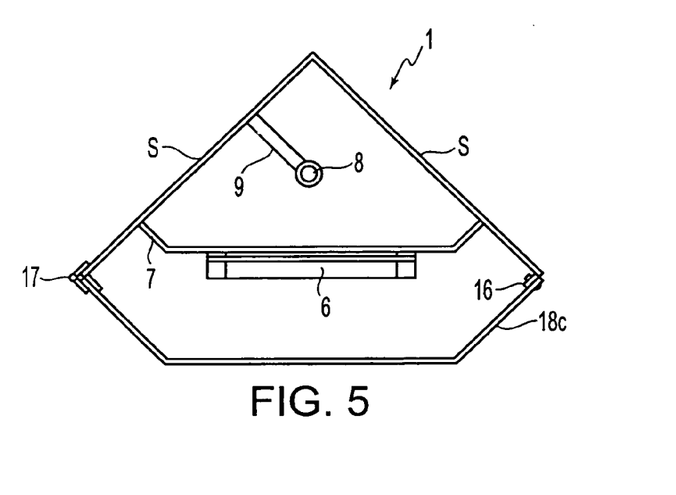
FIG. 5 is a transverse cross-section showing a modification of the Air clean apparatus main body, in which the section is configured in a substantially pentangular shape.

As described above, the section of the Air clean appratus main body 1 is not limited to a fan-shape and it may be formed in either substantially pentangular shape as shown in FIG. 5 or triangular shape (not shown). By forming the Air clean appratus body in such shapes, the Air clean appratus can be placed in the corner of a living room or a bedroom, which is a dead space, as shown in FIG. 1. Thus, unlike Air clean appratuss of the conventional types, the Air clean appratus of the present invention will not be an obstacle even if it is set on a floor or installed on a wall. Note that the Air clean appratus of the present invention may be placed on a place other than the corner, such as the center of a room or a wall side, if desired.

Now, the operation of the present invention will be described below.

Interior air containing floating dusts (substances in particles) sedimented and cumulated on a floor surface and gaseous substances is sucked by the blower being in operation into the Air clean appratus main body 1 through the air intake provided at the lower portion, and the sucked air goes up through and along the anterior filter 5 and the photocatalytic filter 6.

The anterior filter 5 is set to the air intake 3 to capture dusts and some others contained in the sucked air so that the photocatalytic filter 6 at the next stage is prevented from clogging up. Contaminants contained in the sucked air is then oxidized and decomposed on the way that the air moves upward in the Air clean appratus main body through the layer of the photocatalytic filter 6 that is activated by the irradiation of an ultraviolet lamp 8. After the oxidization and decomposition of the contaminants, the air is blown out through the air outlet 4 provided at the upper portion of the Air clean appratus 1 into a room in the form of clean air, effectuating ventilation in the room.

Now, explanation will be made in the following on the details studied for carrying out the present invention.

[Examination 1]

Dusts and substances in particles are naturally sediment within 0.06 to 80 cm/sec in a static space, while they float in a dynamic space. An average speed of walking in a room of a house is 3 to 5 km/hrs, that is, 80 cm/sec. This speed is approximately same as the sedimentation speeds of dusts and substances in particles having a particle size of 50 μm. Therefore, dusts with a size of 50 μm or less will fly, and the amount of dusts that invade and attach to human's respiratory organs will increase. Since all of dusts are not harmful, it is no need to eliminate floating of dusts completely. As a guidepost for eliminating dusts, it is important to control the amount of dust generated per hour and prevent dusts from cumulation. Specifically, ventilation of 1 to several times per hour and, circulation and filtration of air by means of an Air clean appratus is required.

The Air clean appratus is configured in a vertical type that sucks air from the lower portion thereof (Underside-open type) and blows out the sucked air from the upper portion thereof. Floating period of time of particles may be shortened since it depends on the descending airflow speed and the sedimentation speed. Floating period of time may be prolonged when an Air clean appratus of "a transverse airflow type" is used. Since permanently-floating particles are not indebted to the sedimentation speed, the descending airflow speed (ventilation frequency) is increased to thereby shorten the floating/continuance time. Further, an air filter (middle-performance type filter) capable of eliminating particles of the minimum dimension to be eliminated (5 μm in houses) must be used.

[Examination 2]

Particles sedimenting in a static space are cumulated on a floor. An air intake close to a floor surface is effective for suction of cumulated particles. An airflow speed required for rolling particles of the maximum dimension to be eliminated to move on a floor surface will be enough if it is higher than the sedimentation speed. (Friction can be ignored for such a dimension).

When it is supposed that a transverse airflow speed is equal to or higher than a sedimentation speed, in case of an Air clean appratus of an underside-open type with an air intake provided at the under portion, sucked air moves along a floor surface, because three-dimensional attenuation phenomenon of suction force changes to the two-dimensional attenuation. Besides, for sucking particles gathered on a floor surface under the air intake, the upward airflow speed must be greater than the sedimentation speed and the transverse airflow speed. More preferred is that the upward airflow is set to a speed equal to the sedimentation speed (1.5 to 2.0 m/sec), and the upward airflow speed and the transverse airflow speed are then fixed to thereby determine the area of the air intake and the height of the space from the floor surface.

[Examination 3]

For the air outlet, in case of air cleaning-up in houses and a clean room, "height from a floor" and "underside-open area" are determined from a calculation based on particles of the maximum size in a given circulating airflow that must be eliminated at the air intake.

If exterior air is cleaned up and then sucked, pressure in the Air clean appratus will increase, and dusts in the exterior air will not come in. Since dusts and harmful gases stay on the underside, air cleaning-up in such a manner of cleaning up air entered from the underside and blowing out the cleaned-up air from the upper side is carried out. Dusts and pollens are captured by an air filter, harmful gases and odors are oxidized and decompose by the photocatalytic filter, and carbon dioxide and moistures are evacuated. Thus, more clean, contaminants-free and more pleasant air is produced.

The contaminants include gaseous substances and substance in particles. Among the gaseous substances (VOC), substances with dimensions in a range of 0.0001 to 0.0004 μm are gaseous molecules, substances in a range of 0.001 to 0.1 μm are virus, and substance in a range of 0.01 to 0.1 μm or larger are oils and smokes. Among the substances in particles, substances with dimensions of less than 10 μm are invisible with naked eye, and substance of larger than 10 μm are visible. In the substances in particles are included bacteria of 0.5 to 10 μm, spores of moulds of 1.2 to 10 μm more or less, and feces of ticks, pollens, ticks and hairs each with dimensions of larger than 10 μm.

For maintenance of health, intake of gaseous chemical substances into human bodies (especially long-term intakes) must be avoided, and penetration and adhesion of substances in particles into respiratory organs must be avoided. If intake of such substances increases, probability of causing disorder increases. Therefore, ventilation or circular filtration of air must be performed so that cumulation of such substances is prevented from occurring.

As recommendation, the amount of the gaseous chemical substances must be not more than the amount generated per hour. The rate of gaseous chemical substance eliminated by the air filter must be greater than 50% (as particles of the minimum dimensions)) for one time use for one hour. The maximum amount of the gaseous chemical substances must be not more than the cumulation amount during two hours. It is preferred that the said elimination rate of an air filter is greater than 75% (as particles of the minimum dimensions) when the filter is used 0.5 times per hour.

[Method of the Elimination]

From the characteristics of the contaminants, gaseous substances have heavy specific gravities, and they stay on a floor surface excluding carbon dioxide). The gaseous substances move even with a weak airflow and easily diffuse. The substances in particles naturally sediment in a static space and cumulate on a floor surface. The substances in particles easily move and float when receiving airflow at a speed approximately equal to the sedimentation speed. Since the contaminants tend to stay in places of lower levels and move upon receiving a weak airflow, air cleaning-up is preferred to be carried out in a manner that air around a floor surface (containing contaminants in high concentration) is sucked and cleaned up, then the cleaned-up air is blown out from near the ceiling (Downward airflow-type).

As a result, "Effect of accelerating sedimentation of contaminants and shorten the floating period of time thereof" and "Effect of controlling the flying of contaminants" are exerted, allowing to reduce a chance of invasion into human bodies. Carbon dioxide is simultaneously evacuated when the sucked air is evacuated.

[Criteria for Amounts of Substances that should be Eliminated]

| (1) Gaseous substances | |
|---|---|
| $CO_2$ Concentration | 0.1% or less (Buildings Conservation Code) |
| VOC Concentration | 0.08 ppb or less (Building Code) |
| Steam | kg/kg' or less (Building Code) |

(2) Substances in particles

Particles of 5 to 50 μm accord to Weight Code (Building Code)

Particles with a dimension of 50 μm are subject to cleaning-up. Substances in particles with dimensions of 1 to 50 μm float permanently. Sedimentation speed of particles with dimensions of 1, 5, 10 and 50 μm are 0.06, 1.5, 30 and 80 cm/sec, respectively.

Standardized sedimentation speeds (cm/sec) of substances in particles are shown in Table 1.

TABLE 1

| Falling Speed of Substances in Particles (cm/sec) | | | | | | | | | |
|---|---|---|---|---|---|---|---|---|---|
| 1 μm | 2 | 3 | 4 | 5 | 6 | 7 | 8 | 9 | 10 |
| 0.06 | 0.13 | 0.3 | 0.7 | 1.5 | 2.7 | 5 | 9 | 16 | 30 |

(Substances in particles having a sedimentation speed of 1.5 to 30 cm/sec are subject to elimination as to houses.)

| 10 μm | 20 | 30 | 40 | 50 | 60 | 70 | 80 | 100 μm |
|---|---|---|---|---|---|---|---|---|
| 30 | 38 | 49 | 63 | 80 | 100 | 125 | 160 | 200 |

(Substances in particles having a sedimentation speed of 30 to 80 cm/sec are subject to elimination as to houses.)

(Substances in particles having a sedimentation speed of 100 cm/sec or more are subject to cleaning-up.)

Periods of time required for substances in particles to sediment for a distance of CH=2.4 m (height of ceiling) are shown in Table 2.

TABLE 2

Periods of time required for sedimentation for a distance of CH-2.4 m (shortening of floating period of time thanks to descending airflow)

| Dimension | With Natural sedimentation | With descending airflow at a speed equal to sedimentation speed of particle of 1 μm |
|---|---|---|
| Permanent floating | Permanent floating | 240 ÷ 0.06 = 4000 sec. |
| 1 μm | 4000 sec. | 240 ÷ 0.12 = 2000 sec. |
| 5 μm | 160 sec. | 240 ÷ 1.56 = 154.85 sec. |
| 10 μm | 8 sec. | 240 ÷ 30.06 = 7.98 sec. |
| 50 μm | 3 sec. | 240 ÷ 80.06 = 2.9998 sec. |

| Dimension | Ventilation 1 time/hour | Ventilation 3 times/hour | Ventilation 5 times/hour |
|---|---|---|---|
| Permanent floating | 3600 sec. | 1200 sec. | 720 sec. |
| 1 μm | 1890 sec. | 630 sec. | 378 sec. |

TABLE 2-continued

Periods of time required for sedimentation for a distance of CH-2.4 m (shortening of floating period of time thanks to descending airflow)

| | | | |
|---|---|---|---|
| 5 μm | 153.16 sec. | 51.1 sec. | 30.6 sec. |
| 10 μm | 7.98 sec. | 2.7 sec. | 1.6 sec. |
| 50 μm | 2.998 sec. | 1.0 sec. | 0.6 sec. |

Note: The upper limit of the ventilation times is decided based on a descending airflow speed at which spores of moulds with the minimum dimension do not fly. As recommended values, the minimum dimension of mould spores is 3 μm, and sedimentation speed is 0.3 cm/sec which is fixed as the upper limit of the descending airflow speed (the upper limit of the ventilation frequency is 5 times per hour). The maximum value is fixed to 0.7 cm/sec, which is a sedimentation speed of particles of 4 μm. The maximum ventilation frequency is 10 times per hour.

[Walking and Flying of Cumulated Dusts]

Cumulated dusts on a floor roll and move on a floor surface upon receiving airflow caused by walking if the speed of the said airflow is equal to the sedimentation speed of the dusts. If the speed of airflow caused by walking is higher than the said sedimentation speed, the dusts fly at the same speed. Thus, if there is an air intake near a floor surface, the cumulated dusts are moved by the airflow caused by walking and are gradually gathered around the air intake.

| Walking speed | Rolling movement | Flying | Staying |
|---|---|---|---|
| 1 km/H ≈ 30 cm/sec (Standard) | 10 μm | Less 10 μm | Exceed 10 μm |
| 3 km/H ≈ 80 cm/sec | 50 μm | Less 50 μm | Exceed 50 μm |
| 4 km/H ≈ 110 cm/sec | 65 μm | Less 65 μm | Exceed 65 μm |
| 6 km/H ≈ 160 cm/sec | 80 μm | Less 80 μm | Exceed 80 μm |

[Effectiveness of Underside-open Type Air Intake]

Upward Suction Force:

When an upward airflow speed on the surface of the air intake is set to a speed higher than a sedimentation speed of particles of the maximum size that should be eliminated, it is possible to suck particles with dimensions of the said maximum particles or less. Particles with dimensions greater than the dimension of particles of the maximum size are not sucked but cumulate on a floor surface (Subject to cleaning-up).

Distance from Floor Surface to Air Intake:

When the transverse airflow speed is set to a speed equal to a sedimentation speed of particles of the maximum size that should be sucked, particles with dimensions less than the said maximum size roll and move on a floor, float in air, and then sucked. (Friction resistance to a floor is ignored).

Note 1: The maximum size of particles to be eliminated by this method is assignable. Particles smaller than particles of the maximum size are sucked and then eliminated.

Note 2: The minimum size of particles can be assigned based on the eliminating performance of an air filter. Particles of greater than the minimum size are captured and then eliminated.

Artifice: Based on a combination of the above 1 and 2, sizes and a range of sizes of particles that are required to be eliminated or separated can be adopted at will from particles in which large and small particles are intermingled.

[Blowing Out Speed at Air Outlet]

(For prevention from contamination,) the blowing out speed is set at not more than an airflow speed at which particles with a dimension of 10 μm do not fly.

Recommended value: 0.6 m/sec=0.3 m/sec×2

EXAMPLES FOR CALCULATION (1) A case of houses:
Dimension of a room: 5 m×6 m×2.4 mH,
Volume: 72 m$^3$
Ventilation frequency: 1/hour
Circulating air amount: 72 m$^3$/hour
Range of particle dimensions to be eliminated: 5 to 50 μm
  (1) Dimension of air intake: A speed above the suction surface is represented by $V1$, and a speed at a floor surface underneath the air intake is represented by $V2$.
  Dimension of particles of the maximum size is 50 μm, and the sedimentation speed is 80 cm/sec.
  $V1$>0.8 m/sec $V1$=0.8×1.5=1.2 m/sec
  Area of air intake=72÷(1.2×3600)≈0.017 m$^2$
  From this calculated value, 150 mm×113 mm is adopted.
  (2) Height from sucking surface to a floor:
  $V2$≧0.8 m/sec. $V2$=0.8×1.1=0.88 m/sec.
  Circumferential length of air intake=2×(0.15+0.113)= 0.526 m
  Height from sucking surface to floor=72÷(0.88×0.526× 3600)=0.043 m
  From this calculated value, 40 mm is adopted.
  (3) Air filter:
  Dimension of particles of the minimum size is 5 μm.
  PS-400 that can eliminate more than 70% of particles of 5 μm is adopted. (This is equivalent to PS-150+Photocatalyst F)
  (4) Air outlet (V=0.6 m/sec.):
  Area of air outlet=72÷(0.6×3600)≈0.034 m$^2$
  If blown out from three directions, 0.034 m$^2$÷0.376 m=0.09 m, thus, opened distance of 10 cmH is adopted.
  If blown out from two directions, 0.034 m$^2$÷0.263 m=0.13 m, thus opened distance of 15 cmH is adopted.

(2) A case of clean rooms (No class is assigned):
A speed above the sucking surface is represented by $V3$, and a speed on a floor surface underneath the air intake is represented by $V4$.
Dimension of a room: 5 m×6 m×2.4 mH
Volume: 72 m$^3$
Ventilation frequency: 20/hour
Amount of circulating air: 1440 m$^3$/hour
Range of dimensions of particles to be eliminated: 0.5 to 5 μm
  (1) Dimension of air intake:
  Dimension of particles of the maximum size is 5 μm, and the sedimentation speed is 1.5 cm/sec.
  $V3$>1.5 m/sec., thus, $V3$=1.5×1.4=2.1 m/sec.
  Area of air intake=1440÷(2.1×3600)≈0.19 m$^2$
  From this calculated value, 500 mm×380 mm is adopted.
  (2) Height from sucking surface to floor surface:
  $V4$≧1.5 m/sec., thus, $V4$=1.5×1.0=1.5 m/sec.
  Circumferential length of air intake=2×(0.5+0.38)= 1.76 m Height from sucking surface to floor surface=1440÷(1.5× 1.76×3600)=0.152 m From this calculated value, 150 mm is adopted.

(3) Air filter:

Dimension of particles of the minimum size is 0.5 μm, thus, an HEPA filter that can eliminate 99.97% of particles with dimension of 0.5 μm is adopted.

(4) Air outlet (V=0.6 m/sec.):

Area of air outlet=1440÷(0.6×3600)≈0.67 m$^2$

If blown out from three directions, 0.67 m$^2$÷1.26 m=0.53 m, thus, opened distance of 50 cmH is adopted.

If blown out from two directions, 0.67 m$^2$+0.88 m=0.76 m, thus, opened distance of 75 cmH is adopted.

Floating dusts including dusts, spores of moulds, pollens, and corpses and feces of ticks float in air, fall, and are then cumulated. Unlike the conventional circulation-type Air clean appratuss, a vertical-type Air clean appratus is adopted in the present invention, which is configured to suck floating dusts from a floor surface in a room, clean up them and blow out the cleaned-up air together with a large number of minus ions from the upper portion of the Air clean appratus. With a photocatalytic filter installed inside the Air clean appratus, not only exhaust gases and cigarette smokes but also formaldehyde, the cause of so-called sick house, and the like are decomposed. Further, a deodorant system for diffusing scent of forest (phytontide) may be included in the Air clean appratus upon requirement. The Air clean appratus of the present invention cleans up air quickly in silence, fills a room with air with enough freshness, and produces a pleasant and healthy space.

With the Air clean appratus according to the present invention, in which synergistic effect of the photocatalytic filter and minus ions is exerted, dusts, moulds, pollens, feces of ticks and the like are eliminated from air. Hence, a space with pleasant and healthy air is provided. Additionally, the problem of sick house can be resolved. Because, formaldehyde, toluene and the like, that is the cause of sick house, are decomposed and cleaned up by the photocatalytic filter installed in the Air clean appratus of the present invention.

Phytontides (refined vegetable oils) extracted from several tens types of trees thinned out of forests are diffused together with air cleaned-up by the photocatalytic filter, that is the primary function of the present invention, into a room. This system of diffusing phytontides has an effect of quickly neutralize and decompose bad odors generated in a room. Microorganisms, harmful gases and the like attached to the photocatalytic filter (cleanable filter) are decomposed by irradiation of ultraviolet ray. Though the anterior filter (washable filter) can remove dusts, pollens and the like, a red lamp, that indicates the time for cleaning up, will be turned on when it is continuously used for about 30 days. Then, the anterior filter may be washed using a detergent.

As described above, the present invention is directed to an Air clean appratus comprising an air intake intended to be located at a lower position in a corner of a room and an air outlet intended to be located at an upper position in the corner of the room, and at least a filter and a blower both inside the Air clean appratus, characterized in that, when the Air clean appratus is installed in a room, a given quantity of circulating blowing air, the said quantity is decided according to the height from the floor underneath the air intake and the underside-open area determined on the basis of particles of the maximum size to be eliminated at the air intake. Hence, the Air clean appratus of the present invention can eliminate and decompose contaminants including floating dusts having such dimensions that they cumulate on a floor, for example, dusts, hyphae and spores of moulds, pollens, feces of ticks, hairs of pet animals and the like, exhaust gases such as nitrogen and sulfur oxides generated by automobiles, combustion furnaces and the like, those which invade into rooms during ventilation or due to draught. In addition, the Air clean appratus of the present invention can reduce the concentrations in space of totally volatile organic compounds such as formaldehyde, the cause of the recent sick house problem, and keep air in rooms clean.

Further, in the Air clean appratus according to the present invention, since a photocatalytic filter is installed in a direction along the longitudinal axis of the Air clean appratus main body, the Air clean appratus can be configured such that it can be placed in a dead space, for example, in the corner of a room, and that it protrudes just slightly against the interior side, and that it will not be an obstacle after the placement in a room.

What is claimed is:

1. An Air clean apparatus, comprising:
    an air intake intended to be located at a lower position of a corner of a room;
    an air outlet intended to be located at an upper position of the corner of the room;
    at least a filter and a blower both inside the Air clean apparatus, wherein:
        when the Air clean apparatus is installed, a given quantity of circulating blowing air, which is decided according to the height from the floor underneath the air intake and the underside open area determined on the basis of particles of the maximum size to be eliminated at the air intake; and
        a cross-section in side view of the Air clean apparatus as a whole has any shape of substantially fan-shaped, pentangular and triangular.

2. An Air clean apparatus according to claim 1, wherein the both sides of the Air clean apparatus are configured to have a width of at least 180 mm, and a height of 2000 mm or less, respectively.

3. An Air clean apparatus according to claim 1, wherein the blower is configured so that a transverse air flow speed is set to a speed equal to or higher than a sedimentation speed of particles of the maximum size to be eliminated at the air intake.

4. An Air clean apparatus according to claim 1, further comprising at least one lamp extending in a direction along the longitudinal axis of the Air clean apparatus.

5. An Air clean apparatus, comprising:
    an air intake and an air outlet provided in the vicinities of the lower portion and the upper portion of the Air clean apparatus, respectively;
    at least a filter and a blower inside the Air clean apparatus; and
    at least one transverse plate configured to close at least one end side of a photocatalytic filter, wherein:
        when the Air clean apparatus is vertically installed in a room, interior air is sucked by the blower through the air intake and then cleaned up inside the Air clean apparatus, the cleaned air is then blown out through the air outlet to circulate in the room;
        the Air clean apparatus as a whole is formed in a vertically-elongated shape, whose lower portion is located near a floor surface and the upper portion thereof has a height enough to extend up to the vicinity of a ceiling; and
        inside the Air clean apparatus, an anterior filter is provided in the vicinity of the air intake, and the photocatalytic filter having an elongated shape extending in a direction along the longitudinal axis of the Air clean apparatus main body, the photocatalytic filter is adapted to remove and decompose contaminants in the sucked air, is arranged between the anterior filter and the blower.

6. An Air clean apparatus according to claim 5, wherein the both sides of the Air clean apparatus are configured to have a width of at least 180 mm, and a height of 2000 mm or less, respectively.

7. An Air clean apparatus according to claim 5, wherein the blower is configured so that a transverse air flow speed is set to a speed equal to or higher than a sedimentation speed of particles of the maximum size to be eliminated at the air intake.

8. An Air clean apparatus according to claim 5, further comprising at least one lamp extending in a direction along the longitudinal axis of the Air clean apparatus with a distance from a reverse face of the photocatalytic filter.

* * * * *